US011857121B2

(12) United States Patent
Perillo (10) Patent No.: US 11,857,121 B2
(45) Date of Patent: Jan. 2, 2024

(54) PAPER DISPENSER AND METHOD OF USING SAME

(71) Applicant: Louise Ann Perillo, Palm Coast, FL (US)

(72) Inventor: Louise Ann Perillo, Palm Coast, FL (US)

(*) Notice: Subject to any disclaimer, the term of this patent is extended or adjusted under 35 U.S.C. 154(b) by 0 days.

(21) Appl. No.: 17/242,453

(22) Filed: Apr. 28, 2021

(65) Prior Publication Data

US 2021/0267422 A1    Sep. 2, 2021

Related U.S. Application Data

(63) Continuation-in-part of application No. 16/303,836, filed as application No. PCT/US2017/034414 on May 25, 2017, now abandoned.

(60) Provisional application No. 62/342,118, filed on May 26, 2016.

(51) Int. Cl.
| | |
|---|---|
| *A47K 10/38* | (2006.01) |
| *A61L 9/014* | (2006.01) |
| *F21V 33/00* | (2006.01) |
| *F21V 23/04* | (2006.01) |
| *F21Y 115/10* | (2016.01) |
| *A47K 10/36* | (2006.01) |
| *F21Y 103/10* | (2016.01) |

(52) U.S. Cl.
CPC .......... *A47K 10/3836* (2013.01); *A61L 9/014* (2013.01); *F21V 23/0464* (2013.01); *F21V 33/004* (2013.01); *A47K 2010/3668* (2013.01); *F21Y 2103/10* (2016.08); *F21Y 2115/10* (2016.08)

(58) Field of Classification Search
None
See application file for complete search history.

(56) References Cited

U.S. PATENT DOCUMENTS

| | | | | | |
|---|---|---|---|---|---|
| 3,490,578 | A | * | 1/1970 | Speakman | G03C 3/00 206/409 |
| 3,843,071 | A | * | 10/1974 | Graham | B65D 83/0805 206/397 |
| 5,490,625 | A | * | 2/1996 | Myatt | A47K 10/3827 242/596.7 |
| 6,965,205 | B2 | * | 11/2005 | Piepgras | H05B 45/20 315/318 |
| 7,064,498 | B2 | * | 6/2006 | Dowling | H05B 47/155 362/139 |
| 10,334,995 | B1 | * | 7/2019 | Butler | A47K 10/3827 |
| 2006/0006089 | A1 | * | 1/2006 | Arash | A47K 10/16 53/430 |

(Continued)

*Primary Examiner* — William A. Rivera (57) ABSTRACT

A paper dispenser for dispensing paper provided on a roll may include a cylindrical housing having a compartment dimensioned to receive the roll and a slot provided between an inner and an outer surface of the cylindrical housing to dispense paper from the roll. End walls may be removably provided proximate to longitudinal ends of the cylindrical housing. The paper dispenser may also include a decorative layer and a layer of absorptive material for dispensing fragrance. Additionally or alternatively, the dispenser may employ a flexible rod that supports the paper roll in a position that is further away from a support structure than would be possible with a rigid rod, and may provide illumination functionality.

18 Claims, 7 Drawing Sheets

(56) References Cited

U.S. PATENT DOCUMENTS

| | | | | |
|---|---|---|---|---|
| 2006/0043233 A1* | 3/2006 | Borchardt | ............... | B60N 3/00 |
| | | | | 242/593 |
| 2012/0273606 A1* | 11/2012 | Redd | ................. | A47K 10/3818 |
| | | | | 242/588.6 |
| 2014/0027560 A1* | 1/2014 | Flood | ................ | A47K 10/3827 |
| | | | | 242/588.3 |
| 2014/0312048 A1* | 10/2014 | Cojocaru | ............... | A47K 10/38 |
| | | | | 221/45 |
| 2016/0045082 A1* | 2/2016 | Hill | ................... | A47K 10/3836 |
| | | | | 242/596.8 |
| 2016/0198911 A1* | 7/2016 | Ruiz | ..................... | A47K 10/38 |
| | | | | 242/596.7 |

* cited by examiner

PAPER DISPENSER AND METHOD OF USING SAME

CROSS REFERENCE TO RELATED APPLICATIONS

This application is a continuation-in-part of co-pending U.S. patent application Ser. No. 16/303,836, filed Nov. 21, 2018, which claims the benefit of International Application No. PCT/US17/034414, filed May 25, 2017, which in turn claims the benefit of U.S. provisional patent application Ser. No. 62/342,118, filed May 26, 2016; the disclosures of each of the foregoing applications are hereby incorporated herein by reference in their entireties.

FIELD OF THE INVENTION

This invention relates to the field of paper dispensers.

BACKGROUND

In many homes and other environments, paper rolls-such as rolls of toilet paper, power towels, and the like—are kept on horizontal or vertical rods to be dispensed. Unprotected, these rolls are susceptible to being damaged from pets, children, and the elements. Current commercial solutions to store paper rolls in an enclosed environment tend to be stand-alone units, bulky, and may not be able to be used in conjunction with existing structure in a bathroom or kitchen, for example, in residential applications.

BRIEF SUMMARY

The present disclosure provides paper dispensers for dispensing paper provided on a roll that may be used in conjunction with currently existing toilet paper and paper towel holders, and a method of using same.

In accordance with one aspect, the present disclosure provides a paper dispenser for dispensing paper provided on a roll that comprises a cylindrical housing. The cylindrical housing comprises an inner surface defining a compartment therein, the compartment dimensioned to receive the roll, an outer surface defined at an opposing surface to the inner surface, first and second longitudinal ends, the roll insertable into the compartment through either the first or second longitudinal end, and a slot provided between the inner and outer surface and extending longitudinally towards the first and second longitudinal ends. The paper dispenser also comprises first and second end walls, each end wall removably provided proximate to one of the first and second longitudinal ends.

In accordance with another aspect, the present disclosure provides methods of dispensing paper provided on a roll from a paper dispenser. The methods comprise the steps of inserting the roll into a cylindrical housing having first and second longitudinal ends, an inner surface defining a compartment therein, the compartment dimensioned to receive the roll, an outer surface defined at an opposing surface to the inner surface, and a slot provided between the inner and outer surface and extending longitudinally towards the first and second longitudinal ends; securing first and second end walls to the cylindrical housing proximate the first and second longitudinal ends; and dispensing paper from the roll through the slot in the cylindrical housing.

This Brief Summary is provided to introduce a selection of concepts in a simplified form that are further described below in the Detailed Description. This Brief Summary is not intended to identify key features or essential features of the claimed subject matter, or is it intended to be used to limit the scope of the claimed subject matter.

DETAILED DESCRIPTION

Several aspects of the disclosure are described below. It should be understood that numerous specific details, relationships, and methods are set forth to provide a full understanding of the disclosure. One having ordinary skill in the relevant art, however, will readily recognize that the invention disclosed can be practiced without one or more of the specific details or practiced with other methods/protocols. The present disclosure is not limited by the illustrated ordering of acts or events, as some acts may occur in different orders and/or concurrently with other acts or events. Furthermore, not all illustrated acts, steps, or events are required to implement a methodology in accordance with the present disclosure. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The following detailed description and the appended drawings describe and illustrate exemplary embodiments of the disclosure solely for the purpose of enabling one of ordinary skill in the relevant art to make and use the invention. As such, the detailed description and illustration of these embodiments are purely exemplary in nature and are in no way intended to limit the scope of the disclosure, or its protection, in any manner. It should also be understood that the drawings are not to scale and in certain instances details have been omitted, which are not necessary for an understanding of the present invention, such as conventional details of fabrication and assembly.

Embodiments of a paper dispenser for dispensing paper provided on a roll (e.g., a paper roll), in accordance with the disclosure, may include a cylindrical housing. The cylindrical housing may have an inner surface defining a compartment therein, the compartment dimensioned to receive the roll, an outer surface defined at an opposing surface to the inner surface, first and second longitudinal ends, the roll insertable into the compartment through either the first or second longitudinal end, and a slot provided between the inner and outer surface and extending longitudinally towards the first and second longitudinal ends. The cylindrical housing may also have first and second end walls, each end wall removably provided proximate to one of the first and second longitudinal ends.

In one embodiment, the slot may begin at the first longitudinal end and terminate at the second longitudinal end. The end walls may have an outer end wall surface and an inner end wall surface, and an aperture extending between the outer end wall surface and inner end wall surface to receive a rod to support the roll; the rod to support the roll may be flexible as set forth herein. The first and second end walls may be press fit to one of the first and second longitudinal ends. The end walls may include a lip protruding from the inner end wall surface. The lip may have approximately the same diameter as the inner surface of the cylindrical housing and the outer end wall surface may have approximately the same diameter as the outer surface of the cylindrical housing. The paper dispenser may have at least one layer of absorptive material to absorb and disperse a fragrance, the layer of absorptive material provided on at least one of the end walls. In another embodiment, the layer of absorptive material is provided on the outer surface of the cylindrical housing. The paper dispenser may have at least one decorative layer provided on the outer surface of the housing. In another embodiment, the at least one decorative layer is provided on at least one end wall.

In a method embodiment for dispensing paper provided on a roll from a paper dispenser, the method may include the step of inserting the roll into a cylindrical housing having first and second longitudinal ends, an inner surface defining a compartment therein, the compartment dimensioned to receive the roll, an outer surface defined at an opposing surface to the inner surface, and a slot provided between the inner and outer surface and extending longitudinally towards the first and second longitudinal ends. The method may also include the steps of securing the first and second end walls to the cylindrical housing proximate the first and second longitudinal ends, and dispensing paper from the roll through the slot in the cylindrical housing.

In one method embodiment, the first and second end walls may be press fit to one of the first or second longitudinal ends. The roll may be inserted into the compartment through either the first or second longitudinal ends. A rod to support the roll may be inserted thorough an aperture in one of the first or second end walls; in some implementations described below, the rod to support the roll may be flexible such that insertion of opposing ends of the rod into support structures in a roll holder cause the rod to flex or bow along a longitudinal axis. In one method embodiment, a decorative surface may be provided on the outer surface of the cylindrical housing. In another method embodiment the decorative surface may be provided on at least one of the end walls. The method may also include the step of storing a fragrance in at least one layer of absorptive material provided on the outer surface of the cylindrical housing. In another method embodiment, the fragrance is stored in at least one layer of absorptive material provided on at least one of the end walls.

With reference now to FIGS. 1-5, an embodiment of a paper dispenser for dispensing paper provided on a roll 10 is provided in accordance with the disclosure. The paper dispenser 10 may include a cylindrical housing 100 and first and second end walls 200.

Figure 1:
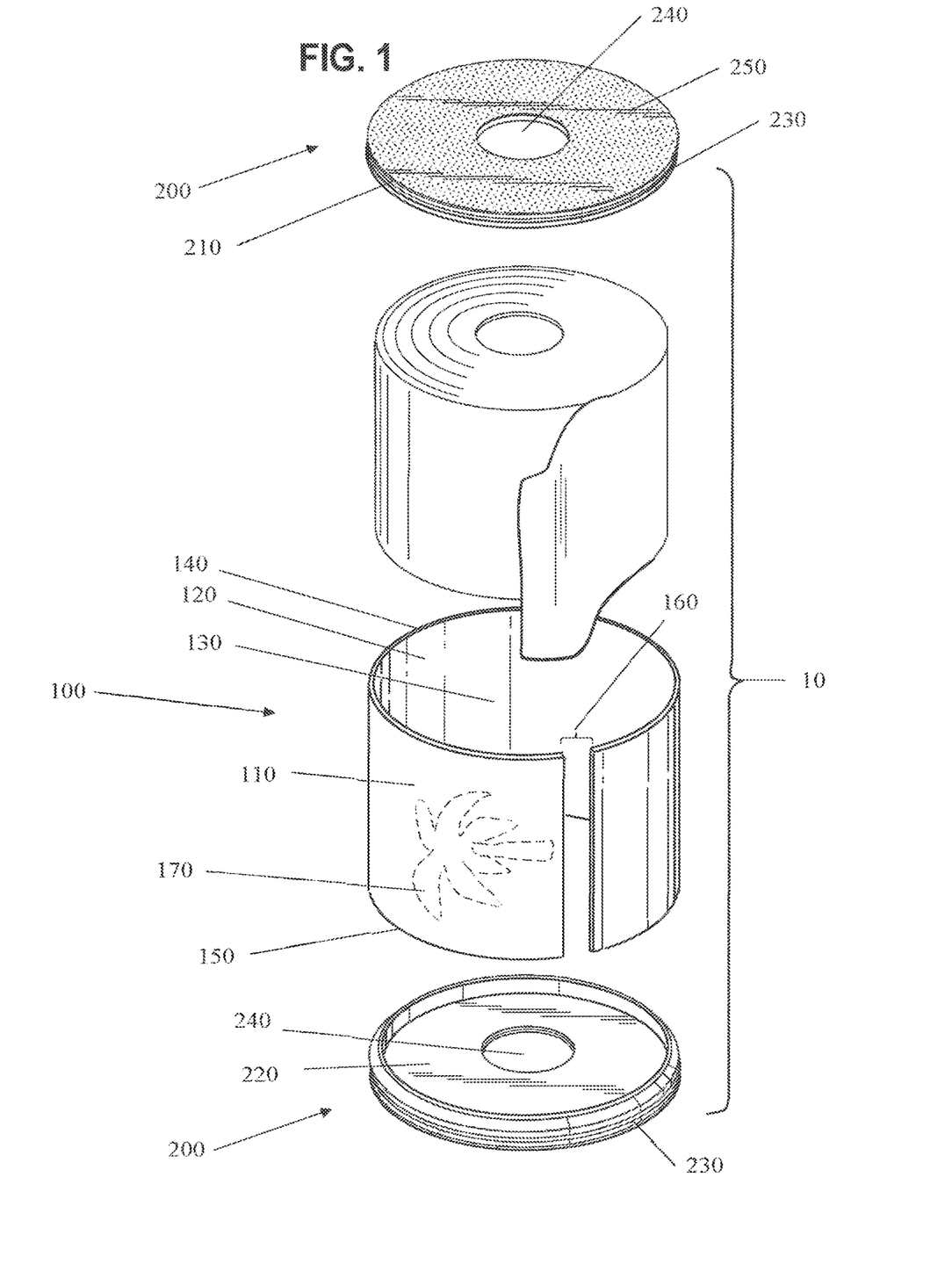
FIG. 1 illustrates an exploded view of an embodiment of a paper dispenser of the present disclosure and a paper roll.
Figure 2:
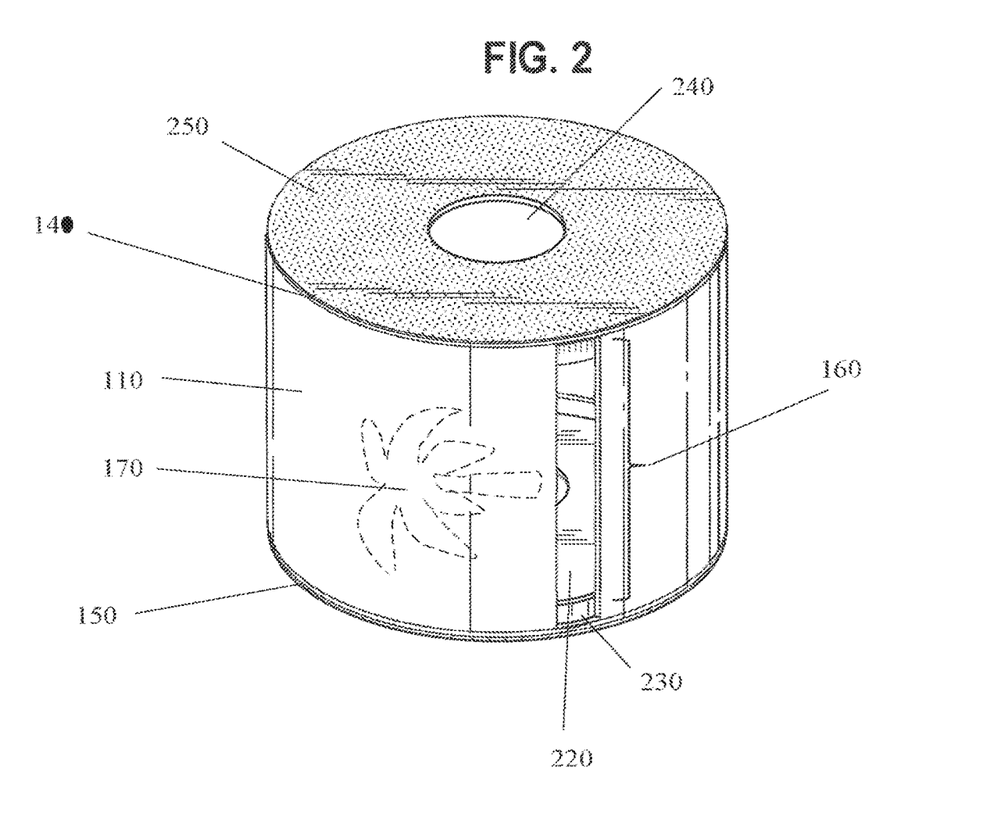
FIG. 2 illustrates a perspective view of an embodiment of the paper dispenser of the present disclosure.
Figure 2A:
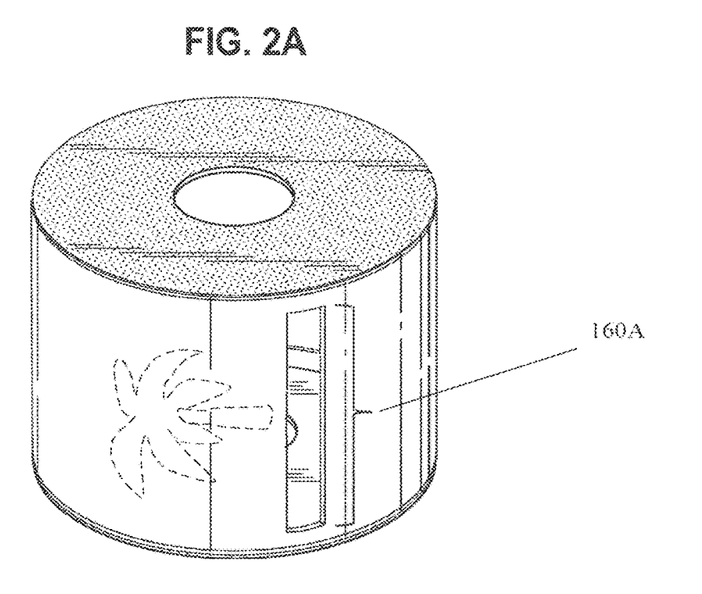
FIG. 2A illustrates a perspective view of another embodiment of the paper dispenser of the present disclosure.
Figure 3:
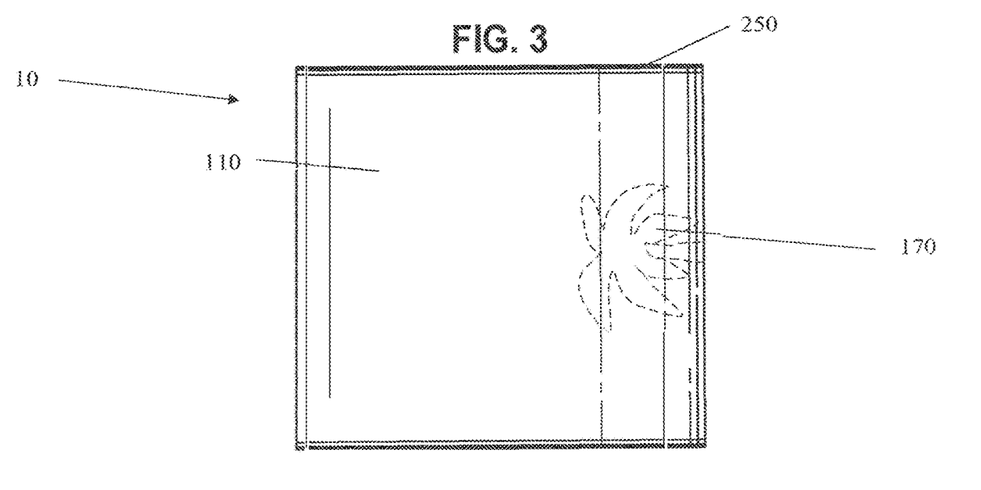
FIG. 3 illustrates a side view of an embodiment of the paper dispenser of the present disclosure.
Figure 4:
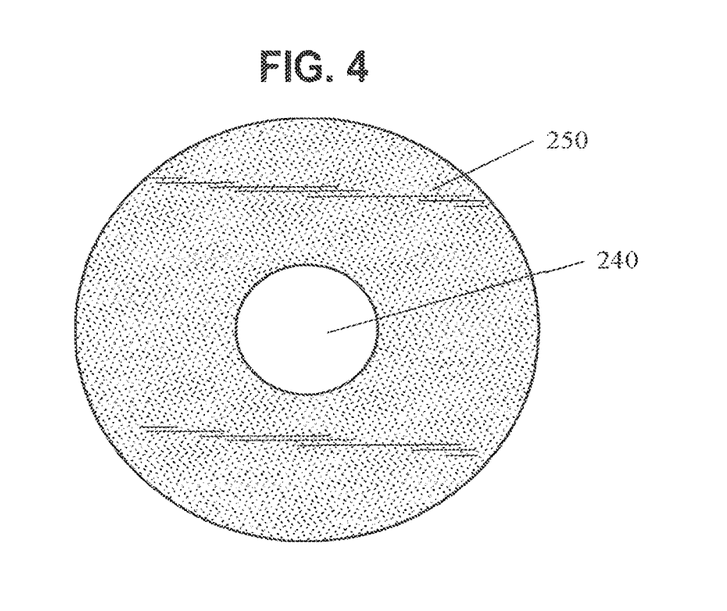
FIG. 4 illustrates a top view of an embodiment of the paper dispenser of the present disclosure.
Figure 5:
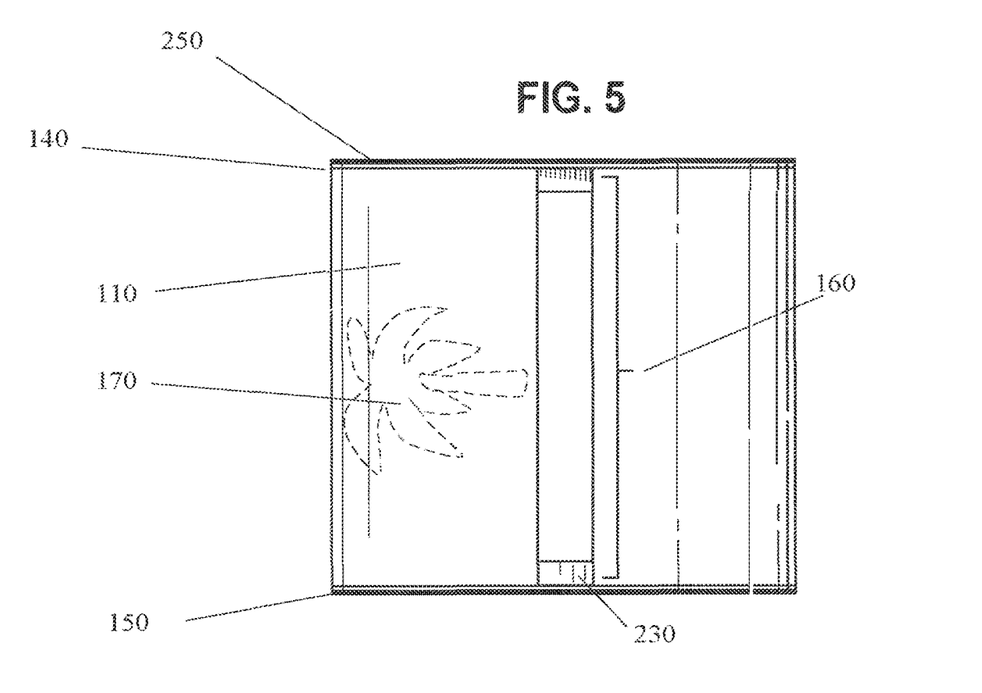
FIG. 5 illustrates a front view of an embodiment of the paper dispenser of the present disclosure.

The cylindrical housing 100 has an outer surface 110, an inner surface 120, a first longitudinal end 140, and a second longitudinal end 150. The inner surface 120 defines a compartment 130 dimensioned to receive a roll, such as a roll of toilet paper or paper towels. However, it may be appreciated that the compartment 130 may receive other types of paper not on a roll, such as tissue paper. Accordingly, the cylindrical housing 100 may be of different diameters and lengths to support the size of the paper product to be dispensed. The cylindrical housing 100 may be substantially constructed from metal, plastic, or any other known or to be developed material suitable for protecting the roll. The first and second longitudinal ends 140, 150 are open such that the roll may be inserted into the compartment 130 through one of the longitudinal ends 140, 150. The cylindrical housing 100 also has a slot 160 between the outer surface 110 and the inner surface 120. As those skilled in the art will appreciate, paper may be dispensed through the slot 160 from the roll that is housed in the compartment 130. As shown in FIG. 1, the slot 160 extends longitudinally from the first longitudinal end 140 to the second longitudinal end 150. However, in another embodiment, shown in FIG. 2A, the slot 160A extends only a portion of the length of the outer surface 110. As those skilled in the art will appreciate, the slot 160A may be longer or shorter to allow the dispensing of various sizes of paper while minimizing the amount of exposure to the roll. As may be appreciated, the cylindrical housing 100 may be operated in a vertical or horizontal position and may hold one or more rolls of toilet paper.

A decorative layer 170 may be provided on the cylindrical housing 100. As shown in FIG. 1, the decorative layer 170 is an image provided on the outer surface 110. However, in another embodiment, the decorative layer 170 is a separate layer, such as a wrap, covering the entire outer surface 110. In yet another embodiment, the decorative layer 170 may be provided on the end walls 200. The decorative layer 170 may be substantially constructed from a fabric, polymers, metal, or any other known or to be developed material suitable for displaying a design. The decorative layer 170 may also incorporate other decorative objects, such as beads, jewels, appliques, stickers, and the like. The decorative layer 170 may be adhered to the outer surface using glue, hook and loop fasteners, or other methods known to those skilled in the art or to be developed. The decorative layer 170 may be removable from the outer surface 110 or end walls 200 to allow a user to change the decorations by adhering other types of wraps (e.g., holiday, personalized, photo, themed etc.) In yet another embodiment, the decorative layer 170 may also be printed onto the outer surface 110 or end walls 200.

As shown in FIG. 1, the first and second end walls 200 have an outer end wall surface 210, an inner end wall surface 220 and the first and second end walls 200 may be removably provided proximate to the first and second longitudinal ends 140, 150, respectively. As those skilled in the art will appreciate, the end walls 200 can be removed to allow the roll to be inserted into the compartment 130 and attached afterwards to enclose the openings at the first and second longitudinal ends 140, 150. The end walls 200 may be cylindrical and have substantially the same diameter as the outer surface 110 of the cylindrical housing 100. However, other dimensions and geometries are contemplated.

In one embodiment, a lip 230 may protrude from the inner end wall surface 220 of at least one of the first and second end walls 200. The lip 230 may have approximately the same diameter as the inner surface 120 of the cylindrical housing 110 such that the end walls 200 may be press fit to the cylindrical housing 110. However, in other embodiments, the end walls 200 are connected to the cylindrical housing 110 using other connection methods and devices, such as hook-and-loop fasteners, latches, nuts and bolts, ball joints, and the like. At least one of the first and second end walls 200 may also include an aperture 240. A conventional paper rod or holder may be inserted into the roll in the compartment 130 through the aperture 240. Alternatively, a flexible rod may be inserted through aperture; engaging each end of such a flexible rod into a paper roll holder may cause the rod to flex or bow, moving cylindrical housing 110 further away from the holder than would be the case if a rigid paper rod were used. As shown in FIG. 1, the aperture 240 is cylindrical in shape to accommodate a cylindrical paper rod or holder, and it may be dimensioned to have a sufficient diameter to accommodate flexure of a flexible rod. However, the aperture 240 may be provided in other dimensions and geometries. In another embodiment, paper, such as tissues, may be dispensed through the aperture 240.

The paper dispenser 10, may also include a layer of absorptive material 250 to absorb and dispense fragrance. The layer of absorptive material 250 may be a porous material such as felt, cotton, wool, or other fabric capable of absorbing a scented liquid. As shown in FIG. 1, the layer of absorptive material 250 is provided on the outer end wall surface 210. In another embodiment, the layer of absorptive material 250 is provided on the outer surface 100 of the cylindrical housing 100.

A method for dispensing paper provided on a roll from a paper dispenser is now described. In one embodiment, the method may include the step of inserting the roll into the compartment 130 of the cylindrical housing 110 through one of the longitudinal ends 140, 150. If attached, the end walls 200 may first be removed. The method may also include attaching the first and second end walls 200 to the cylindrical housing 100 proximate the first and second longitudinal ends 140,150. The paper from the roll may be dispensed through the slot 160 in the cylindrical housing 100. In one embodiment, the first and second end walls 200 may be press fit into one of the first and second longitudinal ends 140, 150. However, other methods of attachment are possible. A rod or holder (which may be rigid or flexible, for example) to support the roll may be inserted through the aperture 240 in one of the first or second end walls 200. The decorative layer 170 may be provided on the outer surface 110 of the cylindrical housing 100. However, in another method embodiment, the decorative layer 170 may be provided on at least one of the end walls 200. Fragrance may be stored in the least one layer of absorptive material 250. The at least one layer of absorptive material 250 may be provided on the outer surface 110 of the cylindrical housing 100. In another embodiment, fragrance is stored in the layer of absorptive material 250 provided on at least one of the end walls 200.

Figure 6A:
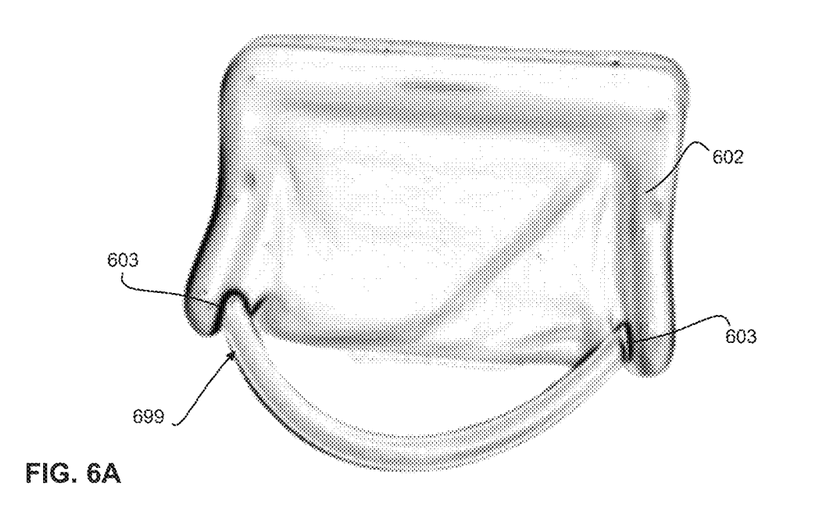
FIG. 6A illustrates a front perspective view and FIG. 6B illustrates a side view of one implementation of a supporting rod for use in connection with the paper dispenser of the present disclosure.
Figure 6B:
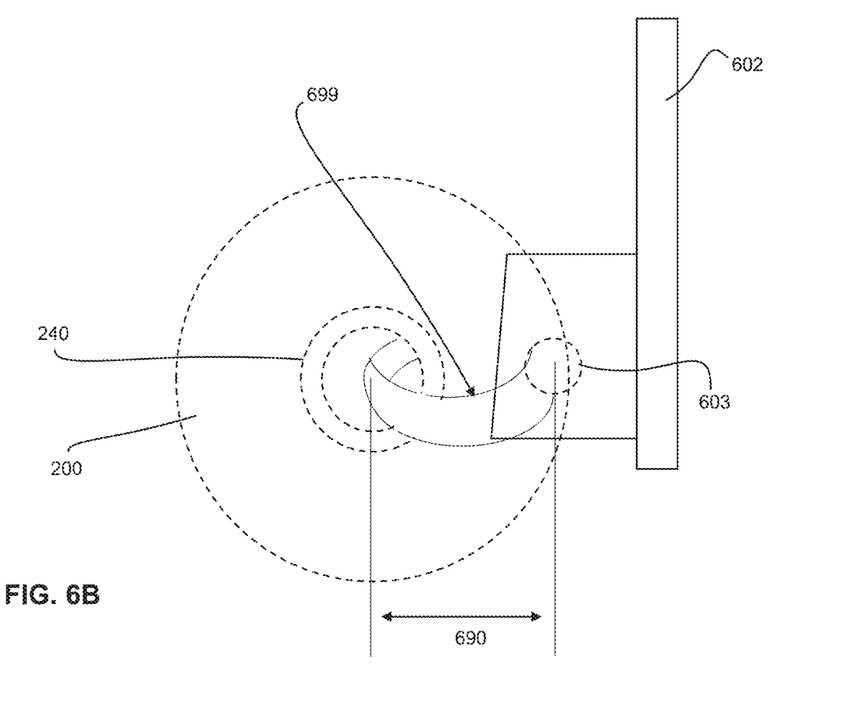
Figure 7:
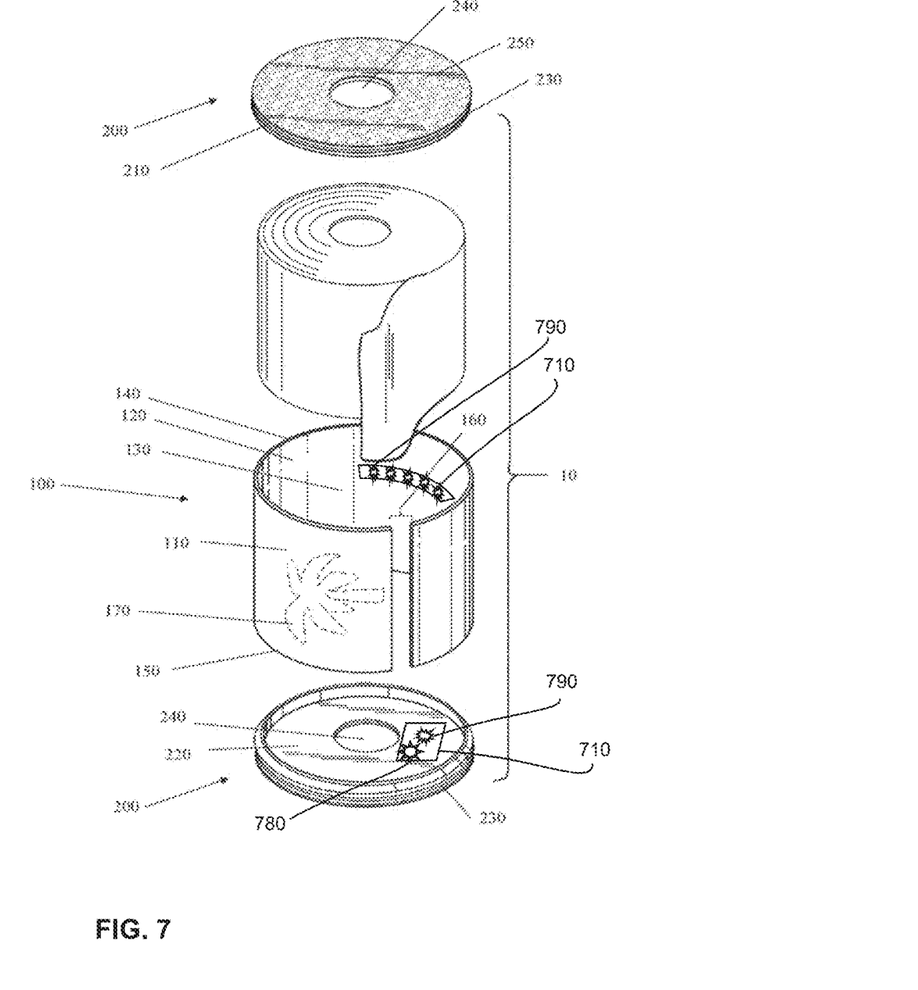
FIG. 7 illustrates an exploded view of the paper dispenser of FIG. 1 including an illumination component.

Turning now to FIGS. 6A through 7, it is noted that FIG. 6A illustrates a front perspective view and FIG. 6B illustrates a side view of one implementation of a supporting rod for use in connection with the paper dispenser of the present disclosure, and FIG. 7 illustrates an exploded view of the paper dispenser of FIG. 1 including an illumination component.

As indicated in FIG. 6A, a holder structure 602 is typically constructed to incorporate or comprise depressions, indentations, or detent mechanisms (reference numeral 603) that are sized and dimensioned to engage ends of a spring-loaded or tension-activated rod that is operative to secure a roll of paper as is generally known in the art. Specifically, structure 602 (usually fabricated of metal or ceramic, for example, as a design choice or for aesthetic reasons) may be attached to a wall, cabinet side, or other support surface, and a rod may be attached and secured at detent mechanisms 603 such that a roll of paper (not illustrated in FIG. 6A) may be supported by and rotate around the rod during dispensing operations. As will be appreciated by those of skill in the art, conventional rods deployed for this purpose are generally rigid, meaning that they describe a substantially linear path between detent mechanisms 603, which may present challenges when a roll of paper that is intended to be supported by the rod exceeds a particular radius.

In a departure from conventional technologies, however, a flexible rod (reference numeral 699) may be employed in lieu of a typical rigid rod. In that regard, a longitudinal axis of flexible rod 699 may be greater than the distance between detent mechanisms 603; as a result, engaging alternate ends of flexible rod 699 with opposing detent mechanisms 603 may generally cause flexible rod 699 to flex or bow away from structure 602, thus providing an increased distance between a longitudinal axis of the paper roll and a face of structure 602; this increased distance is referred to as an "offset," and is best illustrated at reference numeral 690 in FIG. 6B. This offset feature, enabled by flexible rod 699, facilitates paper dispenser 10 accommodating larger rolls of paper than would otherwise have been possible if a rigid rod were used instead of flexible rod 699.

As a practical matter, flexible rod 699 may be constructed of rubber, plastic, fiberglass, carbon fiber or other laminates, textiles or fibrous materials such as bamboo or hemp, or any other pliable material having sufficient malleability and resistance under compression to create offset 690 when opposite ends of flexible rod 699 are engaged with opposing detent mechanisms 603. In that regard, it may be desirable in some instances to select a material and a length of flexible rod 699 as functions of structure 602, in general, and as a function of the distance between detent mechanisms 603, in particular.

As noted above, it will be appreciated that conventional paper support rods are spring-loaded and rigid, such that they do not allow for flexibility with respect to large rolls of toilet paper (or other types of paper), which can be problematic (i.e., such conventional rods do not allow for offset 690 as illustrated in FIG. 6B). Such conventional rods are also limited in color choices, style, and décor, whereas the artistic or aesthetic features of a flexible rod 699 may be limited only by the nature and structural characteristics of the flexible material used in its construction. Furthermore, over time, conventional spring-loaded rods may malfunction (e.g., due to deterioration of the operative spring or failures in the telescoping housings that contain the spring), and need to be replaced; a flexible rod 699, on the other hand, may accommodate a variety of paper roll sizes or diameters, may generally be constructed to fit all or most standard paper holders (such as structure 602), and, due to its one-piece design having no moving parts, may significantly reduce or minimize some of the risks of malfunction over its useful life expectancy. In some commercial implementations, flexible rod 699 may embody or comprise various decorative or functional options such as, but not limited to: fabrication using glow-in-the-dark or bioluminescent materials; independently illuminated versions (such as are described below); decoration or encrustation using colored minerals, rhinestones, beads, crystals, gemstones, and the like; and decorations or other festoonery to match the same, if any, as may be deployed with respect to outer surface 110, to provide a uniform or continuous decorative motif.

As indicated in FIG. 6B, flexible rod 699 may engage detent mechanisms 603 in structure 602; as a consequence of the length and pliant nature of flexible rod 699, engagement of the ends of flexible rod 699 with detent mechanisms 603 may generally cause a flexure or bow in flexible rod 699 away from structure 602. In that regard, due to the aforementioned pliancy of flexible rod 699, an offset (depicted generally, though not to scale, at reference numeral 690) may be created that represents an increase in a distance from a centerline of the paper roll to the centerline of detent mechanisms 603 (and thus, to a bearing surface of structure 602). An effective mechanical offset to allow for a radius of a paper roll, such as offset 690, may allow structure 602 to handle a roll of paper that is larger than a roll that it was designed to accommodate in the first place.

As indicated in FIG. 7, an illumination component 710 may be disposed in one or more of various locations in connection with dispenser 10. By way of example, illumination component 710 may be attached to, adhered to, incorporated into, or integrated with either inner surface 120, inner end wall surface 220, or both (or a combination of same) inside of compartment 130. Both of these implementations are illustrated in FIG. 7, though it is contemplated that these not be utilized simultaneously, and it will also be appreciated that any of various implementations may be employed as a design choice, depending upon the size of the roll of paper to be accommodated in compartment 130, whether electronics and sensors are deployed in connection with illumination component 710, or a combination of these and a variety of other factors.

In some implementations, illumination component 710 may generally comprise a light source 790 and a battery (not shown) to power same, and may optionally comprise a sensor 780 and attendant supporting electronics or data processing resources. In any event, as contemplated by the subject matter disclosed herein, illumination component 710 comprising light source 790 may be disposed (at least partially) inside compartment 130 and may be operative selectively to provide light (from inside compartment 130) to an exterior of compartment 130 via slot 160, apertures 240, or both.

As noted above, aspects or elements of illumination component 710 may be attached to, adhered to, incorporated into, or integrated with inner surface 120, inner end wall surface 220, or both. In some implementations, illumination component 710, or portions thereof, may be welded, braised, soldered, affixed via adhesives, screws, bolts, rivets, or other mechanical fasteners, or otherwise rigidly attached to an appropriate or desired portion of compartment 130 or, optionally, flexible rod 699. In some circumstances, it may be desirable to provide a user of paper dispenser 10 with access to certain functionality of illumination component 710, so a power switch or button (not shown in FIG. 7), for instance, may be provided exterior to compartment 130 (such as on outer surface 110 or on outer end wall surface 210) for convenient access; alternatively, illumination component 710 may be provided with a wireless transceiver (such as a Bluetooth™ or other near-field communications (NFC), wireless, or cellular transceiver) capable of data communications without a wired connection, such that operation of illumination component 710 may be controlled via a remote, wireless device. Additionally or alternatively, in some situations, it may be desirable that illumination component 710 (or at least some components thereof) may be removable from compartment 130, for example, to facilitate replacement of failed incandescent light bulbs, depleted batteries, and the like.

Further, it may be desirable that sensor 780 be employed exterior to compartment 130, and so necessary electrical or data transmission conduits between sensor 780 and other elements of illumination component 710 may be disposed on opposing sides of cylindrical housing 110 or first and second end walls 200, as the case may be. Electrical power connections, data buses, and other electronic infrastructure have been omitted from FIG. 7 for clarity, though it is noted that certain types of wireless transceivers (such as those mentioned above) may be most functional if deployed exterior to compartment 130, such as on outer surface 110 or on outer end wall surface 210. Other elements that are well-known in the art, such as plugs, inputs, or other interfaces for enabling battery charging or for programming of electronics at illumination component 710 are also omitted from FIG. 7 for clarity.

In some implementations, illumination component 710 may be embodied in or comprise a printed circuit board including sufficient control circuitry and other attendant electronics to regulate, manipulate, or otherwise to control operation of light source 790 as set forth herein. In that regard, illumination component 710 may comprise control circuitry (operative under software, for example, or otherwise in accordance with appropriate computer-readable instruction sets) selectively to power light source 790, for instance, as a function of time of day, or responsive to a level of ambient light or other environmental data perceived by sensor 780. Specifically, illumination component 710 may comprise a timer, or have access to a remote source of universal time, such that light source 790 may be selectively activated as a function of time of day in a local time zone. Additionally or alternatively, control circuitry at illumination component 710 may be employed selectively to activate light source 790 as a function of input from sensor 780 (which may be, for example, a motion sensor, a light sensor, an infra-red or heat sensor, a pressure sensor, or the like).

As noted above, light source 790 may be powered by a battery, an appropriately configured capacitor, or other power source (not illustrated in FIG. 7), including, if desired, a source external to dispenser 10 (such as an external alternating current outlet). Such power sources are generally known in the art, however, and the present disclosure is not intended to be limited by the nature or operational characteristics of the power supply employed to provide operating electrical power to light source 790.

Light source 790 may be embodied in or comprise an incandescent light bulb, for example, sized and dimensioned for implementation inside of compartment 130; additionally or alternatively, light source 790 may be a light emitting diode (LED), an organic LED (OLED), or other semiconductor-based component capable of radiating light in a portion of the electromagnetic spectrum that is visible to the human eye. One or more such light sources 790 may be implemented in a linear arrangement, a two-dimensional array, or other configuration, as desired to produce or to provide a desired or required amount of light that is cast from inside compartment 130. For example, in one implementation illustrated near the center of FIG. 7, illumination component 710 is depicted as comprising a plurality of such light sources 790, which may be a plurality of incandescent bulbs or LEDs, depending upon a variety of variables, including desired or required power draw, form factor or other dimensional considerations, heat dissipation characteristics, or a combination of these and other factors. In some instances, a light source 790 implemented as a strip of LEDs may provide light (e.g., to be provided via slot 160, apertures 240, or both) that is suitable for "nightlight" purposes or for a pleasing or desirable aesthetic effect.

Sensor 780 may be as simple as a timer, for instance, which may be synchronized with an external time source or entirely independent and running on a local oscillator. Additionally or alternatively, sensor 780 may be a motion sensor, an aural sensor, a heat or infra-red sensor, a pressure sensor, or an ambient light sensor. For example, sensor 780 may detect the presence of a person in a room, or the proximity of that person to dispenser 10, and control circuitry elements of illumination component 710 may then active light source 790 responsive to input from sensor 780. In one implementation, for instance, sensor 780 may be operable to detect a level of ambient light or sound in a room in which dispenser 10 is deployed, and illumination component 710 may be programmed to activate light source 790 responsive to a level of ambient light or sound, as the case may be, in the room—as a night light, for example, or as a safety feature in hospitals, other medical facilities, schools, and the like.

As noted above, in circumstances in which sensor 780 may acquire data or perceive conditions exterior to compartment 130, it may be desirable to employ sensor 780 on outer surface 110 or on outer end wall surface 210, as opposed to a surface that is interior to compartment 130, depending upon the operational characteristics of sensor 780 and the extent to which alteration of structural components of compartment are to be tolerated.

The descriptions set forth above are meant to be illustrative and not limiting, and persons of skill in the art will recognize that various common and known deviations from the above described structures are considered to be within the scope of the disclosed concepts described herein.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

What is claimed:

1. A paper dispenser for dispensing paper provided on a roll, the dispenser comprising:
    a cylindrical housing comprising
    an inner surface defining a compartment therein, the compartment dimensioned to receive the roll,
    an outer surface defined at an opposing surface to the inner surface,
    first and second longitudinal ends, the roll insertable into the compartment through either the first or second longitudinal end, and
    a slot provided between the inner and outer surface and extending longitudinally towards the first and second longitudinal ends;
    first and second end walls, each end wall removably provided proximate to one of the first and second longitudinal ends; and
    an illumination component comprising a light source, the light source disposed inside the compartment and selectively providing light via the slot; wherein the end walls have an outer end wall surface and an inner end wall surface, and an aperture extending between the outer end wall surface and inner end wall surface to receive a rod to support the roll; wherein the first and second end walls are press fit to one of the fast and second longitudinal ends; and wherein the rod is flexible and bows away from a holder structure when engaged to support the roll.

2. The paper dispenser of claim 1, wherein the slot begins at the first longitudinal end and terminates at the second longitudinal end.

3. The paper dispenser of claim 1, wherein the first and/or second and walls are press fit to one of the first and second longitudinal ends.

4. The paper dispenser of claim 1, further comprising at least one layer of absorptive material to absorb and disperse a fragrance, the layer of absorptive material provided on at least one of the end walls.

5. The paper dispenser of claim 1, further comprising at least one layer of absorptive material to absorb and disperse a fragrance, the layer of absorptive material provided on the outer surface of the cylindrical housing.

6. The paper dispenser of claim 1, further comprising at least one decorative layer provided on the outer surface of the housing.

7. The paper dispenser of claim 1, further comprising at least one decorative layer provided on at least one end wall.

8. The paper dispenser of claim 1, wherein the illumination component comprises a battery to power the light source.

9. The paper dispenser of claim 8, wherein the illumination component comprises an ambient light sensor selectively to power the light source as a function of a level of ambient light.

10. The paper dispenser of claim 8, wherein the illumination component comprises a timer selectively to power the light source as a function of a time of day.

11. The paper dispenser of claim 8, wherein the light source is a bulb.

12. The paper dispenser of claim 8, wherein the light source is a light emitting diode.

13. The paper dispenser of claim 8, wherein the illumination component comprises a plurality of light sources.

14. The paper dispenser of claim 13, wherein the plurality of light sources comprises a light emitting diode strip.

15. A method of dispensing paper provided on a roll from a paper dispenser, the method comprising:
    inserting the roll into a cylindrical housing having first and second longitudinal ends, an inner surface defining a compartment therein, the compartment dimensioned to receive the roll, an outer surface defined at an opposing surface to the inner surface, and a slot provided between the inner and outer surface and extending longitudinally towards the first and second longitudinal ends;
    securing first and or second end walls to the cylindrical housing proximate the first and second longitudinal ends;
    supporting the roll using a rod extending through at least one of the first and second end walls and engaged with a holder structure to support the roll, wherein the rod is flexible and bows away from a holder structure when engaged to support the roll;
    dispensing paper from the roll through the slot in the cylindrical housing; and
    selectively activating a light source disposed inside the compartment thereby providing light via the slot.

16. The method of claim 15, further comprising storing a fragrance in at least one layer of absorptive material provided on the outer surface of the cylindrical housing.

17. The method of claim 15, further comprising the step of storing a fragrance in at least one layer of absorptive material provided on at least one of the end walls.

18. The method of claim 15, wherein the selectively activating comprises utilizing one of a timer and a sensor.

* * * * *